United States Patent [19]

Ichikawa et al.

[11] Patent Number: 5,071,867

[45] Date of Patent: Dec. 10, 1991

[54] TREATMENT OF CHRONIC KIDNEY DISEASE WITH ANGIOTENSIN I CONVERTING ENZYME INHIBITOR

[75] Inventors: Iekuni Ichikawa, Nashville; Agnes Fogo, Mt. Juliet; Masaaki Ikoma; Tetsuya Kawamura, both of Nashville, all of Tenn.

[73] Assignee: Vanderbilt University, Nashville, Tenn.

[21] Appl. No.: 486,133

[22] Filed: Feb. 28, 1990

[51] Int. Cl.$^5$ .............................................. A61K 31/40
[52] U.S. Cl. ................................................... 514/408
[58] Field of Search ......................................... 514/408

[56] References Cited

PUBLICATIONS

*Kidney Int.* 32:794–800, 1987, Beukers et al.
*Kidney Int.* 36:626–635, 1989, Yoshida et al.
*Kidney Int.* 36:969–977, 1989, Brunner et al.
*J. Clinical Invest.* 85:541–549, Feb. 1990, Remuzzi et al.

*Primary Examiner*—Stanley J. Friedman
*Attorney, Agent, or Firm*—Tilton, Fallon, Lungmus & Chestnut

[57] ABSTRACT

A method of healing extracellular matrix degradation to reverse glomerular sclerosis includes the steps of administering on angiotension I converting enzyme inhibitor and suppressing extracellular matrix release independent of the blood pressure effects of the enzyme inhibitor.

2 Claims, No Drawings

TREATMENT OF CHRONIC KIDNEY DISEASE WITH ANGIOTENSIN I CONVERTING ENZYME INHIBITOR

TECHNICAL FIELD

The present invention relates to a method of pharmacologically treating glomerular sclerosis. More specifically, the present invention provides a method of healing extracellular matrix degradation to reverse glomerular sclerosis.

BACKGROUND ART

In the United States alone, it is estimated that 60,130,000 patients have hypertension. Angiotensin I converting enzyme inhibitor (ACEI) are very popular and widely used in treating high blood pressure. These drugs are also often used in the treatment of diabetic kidney disease.

Approximately 12,000,000 people in the United States are estimated to have diabetes. It is already known in humans and animals that ACEI and other blood pressure-lowering drugs have a therapeutic effect on the kidney. The therapeutic effect is limited to only slowing down the effects of the disease. The mechanism of action on the kidney of these drugs is currently believed to be through their effect to lower the systemic pressure (i.e. blood pressure) and the pressures within the kidney micro-circulation. Both fluid pressures are commonly high in humans and animals with chronic kidney disease. Progression of glomerular sclerosis, the medical term for progressive kidney damage, is believed to result from a disruption of the dynamic balance between extracellular matrix synthesis and degradation of the mesangium. Recent in vivo studies by the inventors of the present invention and others have suggested that ACEI's effect of attenuating glomerular sclerosis is independent of its depressor action on systemic and glomerular pressures. Additionally, ACEI's suppressive effect on the extracellular matrix released from cultured mesangial cells has been demonstrated.

In view of the above, applicants have tested and demonstrated a potential benefit on glomerular sclerosis by using ACEI in a dose in excess of that required for normalization of systemic and glomerular pressures. In contrast to commonly held beliefs of the mechanism of action of ACEI, applicant's new observations implicate that patients with chronic renal disease, even without high blood pressure, will benefit from the administration of ACEI, particularly in high doses. This is because of ACEI's therapeutic effect on the kidney independent of its blood pressure controlling effect.

SUMMARY OF THE INVENTION

In accordance with the present invention there is provided a method of healing extracellular matrix degradation to reverse glomerular sclerosis, the method including the steps of administering an angiotensin I converting enzyme inhibitor and suppressing extracellular matrix release independent of the blood pressure effects of the enzyme inhibitor.

DETAILED DESCRIPTION OF THE INVENTION

The present invention provides a method of healing extracellular matrix degradation to reverse glomerular sclerosis. The present invention suggests that glomerular sclerosis is a reversible lesion if the extracellular matrix synthesis is effectively suppressed by therapeutic interventions, such as large doses of ACEI. The ACEI unmasks the healing process of the extracellular matrix degradation. That is, glomerular function status quo is a balance between extracellular matrix synthesis and degradation of the mesangium. This balance is disrupted with the continued progression of glomerular sclerosis. Administration of the ACEI positively effects this balance and reverses the effect of the glomerular sclerosis thereby providing therapeutic intervention of the disease.

Examples of ACEI drugs are Captopril or CAPOTEN, manufactured by Squibb, Enalapril or VASOTEC, manufactured by Merck, Shark and Dohme. These drugs are very popular clinically and widely used in treating high blood pressure. Drugs such as CAPOTEN are normally indicated for use as antihypertensives, effective in the management of heart failure. They are believed to be effective through suppression of the renin-angiotension aldostrone system. However, it is recited in the Physicians' Desk Reference (1990) that there remains no consistent correlation between renin levels and response to the drug.

Captopril has been previously found to be as orally effective converting enzyme inhibitor. Cushman et al, Biochem., 1977, 16, 5484–5491.

As stated above, it is currently believed that their effect to slow down glomerular sclerosis is through their effect to lower the systemic pressure and pressures within the kidney micro-circulation. The present invention is based on evidence implicating that patients with chronic renal disease, even without high blood pressure will benefit from administration of ACEI, particularly in large doses. This is because the therapeutic effect of ACEI is shown on the kidney independent of their blood pressure controlling effect.

Applicant tested the potential benefit on glomerular sclerosis of ACEI in dosages in excess of that required to normalize systemic and glomerular pressures. Eight weeks after the subtotal nephrectomy of Munich M-Wistar rats, the rats were given Enalapril (enalaprilic acid) (ACEI agent) for four weeks of a dose of 50 mg/L drinking water. This is a dose widely used. This group is referred to as sNPX-50, (n=5) or A second group (n=5) was given 200 mg/L, a high dose arbitrarily chosen and is referred to as sNPX-200. A third group of rats, referred to as sNPX-0, were not given any ACEI and served as a control (sNPX-0, n=5). Glomerular sclerosis was semi-quantitatively assessed at biopsy after eight weeks and autopsy after twelve weeks using the sclerosis index of Raij et al. The index is as follows: 0–4 scale: 0=no sclerosis; 4=complete sclerosis.

In the control group, sNPX-0, the sclerosis index increased from biopsy to autopsy, on average by 176 plus±58% (p=0.005). Sclerosis index also increased in the sNPX-50 group, but to a significantly lesser degree, on average by 49±17%. Most remarkably, the sclerosis index decreased markedly and significantly in three sNPX-200 rats by 67–86% (an average fall of 28±30% for all rats).

At 8-12 weeks, both the sNPX-50 and sNPX-200 had systemic and glomerular pressures (approximately 112 mmHg and approximately 52 mmHg respectively), which were indistinguishable from non-nephrectomized rats. This contrasted with the typically elevated values in sNPX-0 rats (approximately 180 mmHg and approximately 63 mmHg, respectively).

The above results suggest the glomerular sclerosis is a reversible lesion if the extracellular matrix release is effectively suppressed by therapeutic interventions, such as large doses of ACEI. The ACEI unmasks the healing process of the extracellular matrix degradation.

The number of people potentially able to benefit from the administration of ACEI, particularly in large doses, is large. Currently, 120,000 people in the United States are on dialysis, while approximately 20,000 have received a transplant a therapy for their chronic kidney disease. The present discovery implicates that ACEI drugs can reverse the progressive kidney damage which is commonly seen in a variety of chronic kidney diseases, while no treatment currently available in humans or animals has this capacity.

At best, current therapy, as mentioned above, may only slow down the inevitable process of entering complete kidney failure, which requires dialysis or kidney transplantation.

The therapeutic effect on the kidney of ACEI which has been demonstrated herein is independent of its blood pressure lowering effect at levels of both the systemic and micro-circularatory pressures. Moreover, in patients with chronic kidney disease accompanying high blood pressures, administration of a large dose of ACEI which is more than the dose necessary to bring blood pressures down to normal levels is worthwhile because of the greater therapeutic effect of such a high dose of ACEI in preventing and reversing kidney disease.

This form of administration of large doses of ACEI is not indicated in current medical practice since even in patients with kidney disease, blood pressure control is the therapeutic goal for the reasons mentioned above.

It is significant to note that the mechanism involved in the action of ACEI controlling high blood pressure through inhibition of angiotensin II (a hormone which is blood pressure raising) synthesis. Therefore, the effect of ACEI in lowering blood pressure is limited to the extent that angiotensin synthesis is inhibited. Since angiotensin II is not absolutely necessary for normal individuals to maintain normal blood pressure, patients can tolerate large doses of ACEI without developing unwanted abnormally low pressure if ACEI is carefully administered in gradually increasing dosage. These patients at the same time would gain a considerable benefit with regard to their kidney disease.

In contrast, it is significant to note that other blood pressure controlling drugs act through more nonspecific mechanism and thereby directly lower blood pressure without limitation. Accordingly, large doses of these other drugs could cause life threatening low blood pressure and cannot be used in this manner. In other words, ACEI has a distinctive therapeutic advantage over other nonspecific antihypertensives since other antihypertensives, such as calcium channel blockers or beta blockers, could not be used in large doses without significant negative hemodynamic effects. On the other hand, ACEI can be used in large doses to achieve maximum to undo organ damage without hemodynamic derangements.

In view of the above, the ACEIs have a therapeutic effect on chronic kidney disease, regardless of their well known effect of controlling high blood pressure. Preferably, these drugs will be given in large doses in excess of what is required for blood pressure control and such large doses can halt and even reverse the progression of renal disease. This therapeutic effect on the kidney independent of its blood pressure effect at large doses, together with expected unique absence of hypertension, will drastically widen the application and change the mode of ACEI administration in kidney diseases. It is further expected that large doses of ACEI may become an effective therapeutic measure to protect other organs, such as the heart in high blood pressure and other abnormal hemodynamic conditions such as heart failure.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A method of healing excessive extracellular matrix in a patient to reverse glomerular sclerosis, said method comprising administering to said patient a dose of an angiotensin I converting enzyme inhibitor in excess of that required for normalization of systemic and glomerular pressure, whereby, extracellular matrix release is suppressed and glomerular sclerosis is reversed, independent of systemic and glomerular pressure effects of the enzyme inhibitor.

2. A method as set forth in claim 1, wherein the inhibitor is selected from the group consisting of captopril and enalopril.

* * * * *

UNITED STATES PATENT AND TRADEMARK OFFICE
CERTIFICATE OF CORRECTION

PATENT NO. : 5,071,867

DATED : December 10, 1991

INVENTOR(S) : Ichikawa et al.

It is certified that error appears in the above-identified patent and that said Letters Patent is hereby corrected as shown below:

Column 1, line 5,

The research carried out in connection with this invention was supported in part by a grant from the National Institutes of Health NIK DK 37868-04 and American Heart Association. The Government and American Heart Association have certain rights in the invention.

Signed and Sealed this

Twenty-sixth Day of September, 1995

Attest:

BRUCE LEHMAN

Attesting Officer

Commissioner of Patents and Trademarks